United States Patent [19]

Jauw

[11] Patent Number: 4,725,434

[45] Date of Patent: Feb. 16, 1988

[54] PROCESS FOR THE PREPARATION OF A FREE FLOWING, HOMOGENEOUS, IODOPHOR CONTAINING WOUND POWDER

[75] Inventor: Tjoe H. Jauw, Amsterdam, Netherlands

[73] Assignee: Euroceltique, S.A., Luxembourg

[21] Appl. No.: 835,759

[22] Filed: Mar. 3, 1986

[30] Foreign Application Priority Data

Mar. 18, 1985 [NL] Netherlands ........................ 8500774

[51] Int. Cl.$^4$ ...................... A61K 31/79; A61K 33/18
[52] U.S. Cl. ........................................ 424/80; 424/150
[58] Field of Search ................................. 424/80, 150

[56] References Cited

U.S. PATENT DOCUMENTS

| | | | |
|---|---|---|---|
| 4,094,967 | 6/1978 | Gilbert | 424/150 X |
| 4,125,602 | 11/1978 | Atasoy et al. | 424/80 |
| 4,214,059 | 7/1980 | Hofer | 424/150 X |
| 4,401,651 | 8/1983 | Knutson | 424/80 |
| 4,576,818 | 3/1986 | Shetty | 424/150 |

*Primary Examiner*—Leonard Schenkman
*Attorney, Agent, or Firm*—Steinberg & Raskin

[57] ABSTRACT

A free flowing iodophor powder which can be used for the treatment of wounds and the like, is prepared by spraying a solution of the iodophor in an aqueous-alcoholic solvent having a boiling point at normal pressure of less than 100° C. into a fluidized bed of a finely divided sugar. This results in the formation of a free flowing powder which is well tolerated upon application to wounds.

19 Claims, No Drawings

PROCESS FOR THE PREPARATION OF A FREE FLOWING, HOMOGENEOUS, IODOPHOR CONTAINING WOUND POWDER

BACKGROUND OF THE INVENTION

Iodophors are physiologically acceptable complexes of iodine with certain organic polymers, as for example polyvinylpyrrolidone (povidone), in which the germicidal and microbicidal activity of the elemental iodine is maintained. In general, the useful iodophors are water soluble.

The organic polymers used to form an iodophor comprise a broad range in molecular weight and chain length, and may be either ionic or nonionic in character, as well as possessing either surfactant or non-surfactant properties. A loose bond forms between the iodine and organic polymer to form the complex or iodophor, and aqueous solutions of up to 30% by weight of iodine content may be prepared (all percents are by weight herein, except as otherwise noted).

The general class of organic iodophor compounds comprises two distinct polymer groups: povidone, and polydextrose, which are nondetergent, nonionic and nonsurface active polymers; and a broad variety of detergent/surface-active polymers including nonionic, anionic, and cationic surface active polymers. Both polymer groups are complexed with elemental iodine to form the iodophor. Anionic surface active agents are generally not capable of providing stable iodine complexes. However, certain anionic surface active agents, such as enumerated in U.S. Pat. No. 3,039,916, have been found to be suitable for forming iodine complexes for germicidal use. Povidone-iodine is the most effective and most widely used iodophor and for many years was substantially the only nondetergent, nonionic iodophor which has been found to be suitable for germicidal action in man and animals, has well as in environmental uses. The preparation of povidone iodine has been described in U.S. Pat. No. 2,739,922 and elsewhere.

Polydextrose iodine is a new nonionic, nonsurface active iodophor which has also been found to be highly effective, and the preparation and use thereof is described in U.S. Pat. No. 4,576,818.

The iodophors, and particularly povidone iodine and polydextrose iodine, are dispensed in various kinds of semisolid and liquid pharmaceutical preparations, such as solutions, ointments and aerosols. In the treatment of wounds, however, a powder formulation is desirable because of ease of application, namely simple sprinkling of the powder into and onto the wounds. For best results, such powder should be both homogeneous and free flowing.

However, the iodophors, and particularly the non-ionic, nondetergent iodophors such as polydextrose iodine and povidone iodine, are amorphous, hygroscopic and nonfree flowing powders. They can be transformed into free flowing powders by the addition of glidants, such as talc. However, although talc is widely used as a dusting powder and is an innocuous substance when applied to the intact skin, it can induce severe granulomatous reactions when introduced into wounds or when applied during surgery. Consequently, powders of this type cannot be used for such purposes as the treatment of wounds.

Thus, there has been a need for developing a free flowing iodophor in powder form which does not contain a glidant such as talc and which can be applied to wounds and the like.

SUMMARY OF THE INVENTION

It is according a primary object of the present invention to provide for the production of a free flowing iodophor powder which can be used for the treatment of wounds.

It is another object of the present invention to provide a method of producing iodophors in free flowing powder form which can be applied to open wounds.

Other objects and advantages of the present invention will apparent from the further reading of the specification and of the appended claims.

With the above and other objects in view, the present invention mainly provides for the production of a free flowing iodophor-containing powder that can be applied to wounds, the method comprising spraying a solution of an iodophor in an aqueous-alcoholic solvent having a boiling point of 760 mm Hg, of less than 100° C. into a fluidized bed of a finely divided sugar.

The invention is applicable to all iodophors including the detergent iodophors and the nondetergent iodophors. The invention is particularly applicable for polydextrose iodine and povidone iodine, and according to the preferred embodiment of the present invention the process is used for the preparation of a povidone iodine powder.

The sugar used for the process of the present invention can be any solid saccharide that can be finely divided enough to form a free flowing powder. The disaccharides are particularly preferred, including sucrose, dextrose, maltose, fructose and lactose. The most preferred sugar is sucrose.

The finely divided sugar may have any suitable range of particle size, that is suitable for the formation of a finely divided powder that can be applied to wounds. Preferably, all of the sugar particles should have the size of 250 microns or less (60 mesh sieve) with at least 90% of the sugar particles having a particle size of 150 microns or less (100 mesh sieve).

Povidone iodine, the preferred iodophor, is a highly effective germicide, providing a broad spectrum of microbiocidal action against virtually all microbes. It may be prepared by any of a number of known routes, see, for example, European Published Application Nos. 120301A and 6340A and British Patent No. 1580596, the contents of which references are incorporated herein by reference.

Polydextrose is a non-nutritive polysaccharide, prepared by the condensation polymerisation of saccharides in the presence of polycarboxylic acid catalysts, under reduced pressure. Polydextrose is described in U.S. Pat. Nos. 3,766,105 and 3,786,794, and is available from Pfizer Inc., New York. Commercially available polydextrose polymer is a low molecular weight, water-soluble, randomly bonded polymer of glucose containing minor amounts of sorbitol end groups and citric acid residues attached to the polymer by mono- or di-ester bonds. The number average molecular weight of this commercially available material is 1,500, ranging from about 160 to about 20,000.

When polydextrose polymer is combined with elemental iodine, preferably in the presence of an alkali metal iodide, the resultant polydextrose iodine complex is formed. This complex is a tan-to-amber colored product which melts between 90° C. and 130° C. to form a red liquid. Polydextrose iodine powder is highly soluble in water and at room temperature results in a reddish brown colored aqueous solution.

The amount of iodine incorporated into the iodophors used according to the present invention is determined by many factors. Preferably, the iodine content is between about 1–20% by weight and most preferably about 2–15% by weight of the iodophor dry weight.

The concentration of the iodophor in the present wound powder will depend on the antibacterial strength required. In addition, iodophor concentration will be determined by, among other factors, the iodophor employed, the propensity of the iodophor to cause irritation and the amount of iodine in the iodophor.

Thus, the wound powder preferably contains enough iodophor to afford a concentration of available (titratable) iodine within the powder of between 0.1 and 2% (by weight), especially between 0.2 and 1.5% (by weight).

Thus, a wound powder employing povidone iodine, with 10% (by weight) available iodine, as the iodophor, would preferably contain between 1 and 20%, especially 2 and 15%, (by weight) of povidone iodine.

Any alkyl alcohol having a boiling point, at 760 mm Hg, below 100° C., may be employed in the present process. Alkyl alcohols, such a methanol, ethanol and isopropanol, having a boiling point (at 760 mm Hg) below 90° C. are preferred, with ethanol being particularly preferred.

Any ratio of alcohol to water in the solvent can be used to produce a free-flowing wound powder by the present process. The ratio is chosen so that the evaporation of the solvent is neither too slow nor too rapid. If the evaporation is too slow it leads to sticky products, whereas, if it is too rapid, it leads to non-homogeneous products. It has been found that the most effective solvent for use in the present process contains between 70% and 85% (v/v) alkyl alcohol and between 30% and 15% (v/v) water, especially between 78% and 80% (v/v) alkyl alcohol and between 22% and 20% (v/v) water.

The iodophor solution may also contain selected pharmaceutical excipients that will facilitate the removal of the subsequent wound powder from a wound for cleansing or inspection purposes. These excipients are preferably free flowing powders and are water soluble. Examples include polyethylene glycol and certain celluloses, e.g. carboxyalkylcelluloses and hydroalkylcelluloses.

The present process may be conducted at any temperature that leads to a free-flowing wound powder. In a preferred embodiment of the present invention, the process is conducted at a temperature between 30° C. and 50° C., especially at about 40° C.

It is an important feature of the present process that the pH of the subsequent iodophor-sugar combination may be adjusted to a value that is well tolerated in the treatment of wounds. Well tolerated iodophor/sugar powders will produce 50% (w/v) aqueous solutions that have a pH between 3.0 and 7.0, especially between 4.0 and 6.0.

This adjustment may be effected by the addition of a base to the iodophor solution prior to spraying. In a particularly preferred embodiment of the present process, a solution of povidone iodine in aqueous ethyl alcohol is neutralized with sodium hydroxide solution. In this embodiment, once the process is complete, a 50% (w/v) aqueous solution of the subsequent povidone iodine/sucrose powder has a pH between 4.5 and 5.0. It is therefore well tolerated when sprayed on open wounds.

Such an adjustment is not possible when the wound powder is prepared by conventional granulation methods or if an iodophor/ sugar mixture is sprayed with dilute alcohol in a fluidized bed granulator. In these cases, a 50% (w/v) aqueous solution of subsequent povidone iodine/sucrose powder has a pH value of 1.5. The powder would therefore not be well tolerated when sprayed on an open wound.

The production of a free flowing wound powder by the present process is surprising because (a) no conventional granulation techniques are employed, that is mixing an iodophor (especially povidone iodine) and a sugar (especially sucrose) in a suitable granulator with the aid of an aqueous alcohol, subsequent drying and sieving produces a powder of insufficient homogeniety and fineness for wound treatment, and (b) furthermore, when a mixture of an iodophor (especially povidone) and a sugar (especially sucrose) are sprayed with an aqueous alcohol in a fluidized bed granulator the product is once again non-homogenous and too coarse.

Wound powders prepared by the present process may be dispersed freely onto skin or wounds to the skin. In order to facilitate the use of the present wound powders, however, they may be coated or admixed with other ingredients, such as free flowing powders, that are adapted to improve the therapeutic nature of the powder. Examples of such additional powders include (i) Polyethylene glycol, a carboxyalkylcellulose or a hydroxyalkylcellulose. These facilitate the removal of the wound powder of the present type from a wound when it (the wound) has to be cleaned or inspected, (ii) Zinc oxide. This material possesses mild astringent and antiseptic properties in its own right and therefore acts so as to aid the healing of skin wounds. Zinc oxide also improves the powder flow characteristics of the present wound powders.

Wound powders of the present invention are conveniently dispersed or sprinkled onto an area of skin to be treated from a bottle having a plurality of small holes at its outlet, such as the type of bottle that is generally used for the application of talcum powder. Preferably the bottle used is made of a flexible or resilient material so that the bottle may be squeezed to help expel the powder.

DESCRIPTION OF PREFERRED EMBODIMENTS

The following examples are given to further illustrate the present inventon. The scope of the invention is not, however, meant to be limited to the specific details of the examples.

Preparation of Polydextrose Iodine Powder

Polydextrose (0.84 kg) was dissolved in warm water (10 liters). A solution of iodine (103 gm) and ammonium iodide (57 gm) in ethanol (3 liters) was added. After stirring for 1 hour at 20° C., the solvents were evaporated, under reduced pressure, and the residue was pulverized.

EXAMPLE 1

Finely divided sucrose (4.5 kg) was brought into a fluidized bed granulator at 40° C. Povidone iodine (0.5 kg) was dissolved in a mixture of 96% ethanol (3.5 liters) and distilled water (0.75 liters). This solution was neutralized with 4N sodium hydroxide solution and then sprayed onto the sucrose powder at a rate of 50 ml min$^{-1}$ and at a spraying pressure of 4 bar ($4\times10^5$ Pascals).

The granulate obtained was sieved through a 60 mesh sieve in order to remove any coarse particles. The yellow-brown, free-flowing, homogeneous powder has a particle size distribution as follows:

| | |
|---|---|
| 60 mesh, | 4% (by weight) |
| 80 mesh, | 9% |
| 100 mesh, | 43% |
| 120 mesh and finer, | 44% |

EXAMPLE 2

The process of Example 1 was repeated except that polydextrose iodine (0.4 kg) replaced the povidone iodine.

EXAMPLE 3

The process of Example 1 was repeated except that finely divided lactose (4.5 kg) replaced sucrose as the sugar.

EXAMPLE 4

The process of Example 1 was repeated except that finely divided dextrose (2.3 kg) replaced sucrose as the sugar.

EXAMPLE 5

Finely divided sucrose (4.8 kg) was brought into a fluidized bed granulator at 40° C. Povidone iodine (0.6 kg) was dissolved in 96% ethanol (3.5 liters) and a solution of polyethylene glycol 6000 (0.6 kg) in distilled water (0.5 liters) was added. This solution was neutralized with 4N sodium hydroxide to pH 7.0 and then sprayed onto the sucrose powder at a rate of 50 ml min$^{-1}$ and at a spraying pressure of 4 bar ($4\times10^5$ Pascals).

While the invention has been illustrated with respect to particular iodophors and sugars, it is apparent that variations and modifications of the invention can be made without departing from the spirit or scope thereof.

What is claimed is:

1. Method of preparing a homogenous, free flowing powdered iodophor, which comprises introducing a finely divided sugar into a fluidized bed granulator to form a fluidized bed of said finely divided sugar, spraying a solution of an iodophor in an aqueous-alcoholic solvent having a boiling point at 760 mm Hg of less than 100° C. into said fluidized bed of said finely divided sugar, whereby a homogenous, free flowing powder is formed containing said iodophor, which powder can be applied to wounds and the like.

2. Method according to claim 1 wherein the sugar is a disaccharide.

3. Method according to claim 1 wherein the sugar is sucrose, dextrose, maltose, fructose or lactose.

4. Method according to claim 1 wherein the sugar is sucrose.

5. Method according to claim 1 wherein the sugar has a particle size of 250 microns or less with at least 90% thereof having a particle size of 150 microns or less.

6. Method according to claim 1 wherein the iodophor is polydextrose iodine or povidone iodine.

7. Method according to claim 1 wherein the iodophor is povidone iodine.

8. Method according to claim 1 wherein the iodine content of the iodophor is adjusted to an amount such that the resulting powder contains between 0.1 and 2.0% by weight of iodine.

9. Method according to claim 8 wherein the amount of iodine is between 0.2 and 1.5% by weight.

10. Method according to claim 1 wherein the alcohol is an alkyl alcohol.

11. Method according to claim 1 wherein the alcohol is methanol, ethanol or isopropanol.

12. Method according to claim 1 wherein the alcohol is ethanol.

13. Method according to claim 1 wherein the solvent contains 70-95% by volume of an alkyl alcohol and between 30 and 15% by volume of water.

14. Method according to claim 13 wherein the amount of alkyl alcohol is 78-80% by volume and the amount of water is 22-20% by volume.

15. Method according to claim 1 wherein the pH of the iodophor solution prior to spraying is adjusted to a value such that a 50% weight to volume aqueous solution of the resulting powder has a pH of between about 3.0 and 7.0.

16. Method according to claim 15 wherein the pH value is between 4.0 and 6.0.

17. The free flowing powdered iodophor produced by the process of claim 1.

18. Method according to claim 1 wherein the resulting powder is mixed with polyethylene glycol, a carboxyalkylcellulose, a hydroxyalkylcellulose or zinc oxide.

19. The free flowing iodophor powder produced by the method of claim 18.

* * * * *